(12) United States Patent
Hershberger et al.

(10) Patent No.: US 8,088,291 B2
(45) Date of Patent: Jan. 3, 2012

(54) METHOD OF COLLECTING MEDICAL WASTE IN A WASTE COLLECTION UNIT USING DISPOSABLE MANIFOLD WITH STAGED WASTE FILTERING/PROCESSING

(75) Inventors: David Hershberger, Kalamazoo, MI (US); Richard F. Huyser, Kalamazoo, MI (US); Stephen P Isham, Kalamazoo, MI (US); Bruce MacDonald, Kalamazoo, MI (US); Michael Noonan, Kalamazoo, MI (US); Karen Staley, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 12/393,573

(22) Filed: Feb. 26, 2009

(65) Prior Publication Data

US 2009/0159535 A1 Jun. 25, 2009

Related U.S. Application Data

(62) Division of application No. 11/060,977, filed on Feb. 18, 2005, now Pat. No. 7,497,340.

(60) Provisional application No. 60/545,974, filed on Feb. 19, 2004.

(51) Int. Cl.
*B01D 35/00* (2006.01)
*B01D 36/00* (2006.01)
*B01D 35/28* (2006.01)
*B01D 37/00* (2006.01)

(52) U.S. Cl. .......... 210/767; 210/86; 210/130; 210/136; 210/248; 210/323.1; 210/406; 210/435; 210/452; 210/448

(58) Field of Classification Search .................. None
See application file for complete search history.

(56) References Cited

U.S. PATENT DOCUMENTS

| | | |
|---|---|---|
| 110,136 A | 12/1870 | Hemenway |
| 493,378 A | 3/1893 | Gibson |
| 1,930,590 A | 10/1933 | Ebinger |
| RE24,255 E | 12/1956 | Lund |
| 3,060,882 A | 10/1962 | Peters et al. |
| 3,084,634 A | 4/1963 | McDougall |
| 3,085,689 A | 4/1963 | Hering et al. |
| 3,295,686 A | 1/1967 | Krueger |
| 3,415,485 A | 12/1968 | Hirs et al. |
| 3,469,700 A | 9/1969 | Johnson |
| RE27,399 E | 6/1972 | Urso |

(Continued)

FOREIGN PATENT DOCUMENTS

WO 9933501 7/1999

*Primary Examiner* — Benjamin Kurtz
(74) *Attorney, Agent, or Firm* — Howard & Howard Attorneys PLLC

(57) ABSTRACT

A method of collecting medical waste in a waste collection unit using a disposable manifold and filter assembly. The disposable manifold and filter assembly includes a manifold housing with a plurality of inlets, a neck extending from the manifold housing to define an outlet, and a filter basket disposed in the manifold housing. The method includes inserting the neck into the waste collection unit to direct the medical waste passing through the disposable manifold and filter assembly into the waste collection unit. Tubes are connected to the inlets of the manifold housing to provide a path for the medical waste to travel from a target site, e.g., a patient, to the manifold housing. A vacuum is drawn in the waste collection unit to pull the medical waste through the tubes and into the disposable manifold and filter assembly where the medical waste is processed/filtered in a plurality of stages.

4 Claims, 16 Drawing Sheets

U.S. PATENT DOCUMENTS

| | | |
|---|---|---|
| 3,780,867 A | 12/1973 | Zirtis |
| 4,141,379 A | 2/1979 | Manske |
| 4,226,344 A | 10/1980 | Booth et al. |
| 4,322,054 A | 3/1982 | Campbell |
| 4,443,336 A | 4/1984 | Bennethum |
| 4,642,089 A | 2/1987 | Zupkas et al. |
| 4,655,754 A | 4/1987 | Richmond et al. |
| 4,735,610 A | 4/1988 | Akkas et al. |
| 4,775,469 A | 10/1988 | Zimmerly |
| 4,880,411 A | 11/1989 | Fangrow, Jr. et al. |
| 4,915,688 A | 4/1990 | Bischof |
| 4,957,492 A | 9/1990 | McVay |
| 4,999,109 A | 3/1991 | Sabre |
| 5,100,541 A | 3/1992 | Kallenbach |
| 5,251,664 A | 10/1993 | Arvidsson et al. |
| 5,308,483 A | 5/1994 | Sklar et al. |
| 5,441,650 A | 8/1995 | Kirsgalvis |
| 5,503,740 A | 4/1996 | Callaghen et al. |
| 5,637,103 A | 6/1997 | Kerwin et al. |
| 5,707,535 A | 1/1998 | Harris |
| 5,914,047 A | 6/1999 | Griffiths |
| 5,945,004 A | 8/1999 | Ohira et al. |
| 5,971,956 A | 10/1999 | Epstein |
| 5,997,773 A | 12/1999 | Wilbur et al. |
| 6,024,720 A | 2/2000 | Chandler et al. |
| 6,083,205 A | 7/2000 | Bourne et al. |
| 6,139,757 A | 10/2000 | Ohmura et al. |
| 6,149,812 A | 11/2000 | Erickson |
| 6,180,000 B1 | 1/2001 | Wilbur et al. |
| 6,222,283 B1 | 4/2001 | Regla |
| 6,244,311 B1 | 6/2001 | Hand et al. |
| D446,791 S | 8/2001 | Beckham |
| 6,331,246 B1 | 12/2001 | Beckham et al. |
| 6,562,233 B1 | 5/2003 | Schilling et al. |
| D479,744 S | 9/2003 | Mallett et al. |
| 6,733,664 B2 | 5/2004 | Menne et al. |
| 2003/0042187 A1 | 3/2003 | Menne et al. |
| 2004/0016691 A1 | 1/2004 | Smit et al. |
| 2004/0060856 A1 | 4/2004 | Weigeldt et al. |

METHOD OF COLLECTING MEDICAL WASTE IN A WASTE COLLECTION UNIT USING DISPOSABLE MANIFOLD WITH STAGED WASTE FILTERING/PROCESSING

RELATED APPLICATIONS

This application is a divisional of application Ser. No. 11/060,977, filed on Feb. 18, 2005, which claims the benefit of U.S. Provisional Patent Application No. 60/545,974, filed Feb. 19, 2004, the advantages and disclosures of each of which are hereby incorporated by reference.

FIELD OF THE INVENTION

The present invention relates generally to a method of collecting medical waste in a waste collection unit. More specifically, the present invention relates to a method of collecting medical waste in the waste collection unit using a disposable manifold and filter assembly to direct and filter medical waste, e.g., bodily fluids and materials, entering the waste collection unit.

BACKGROUND OF THE INVENTION

Waste collection units are well known for use in surgical environments to collect medical waste such as bodily fluids and materials during a surgical procedure. Examples of waste collection units can be found in U.S. Pat. Nos. 5,997,733; 6,180,000; and 6,222,283. For instance, U.S. Pat. No. 5,997,733 discloses a waste liquid and smoke disposal system which combines the functions of a smoke extraction system and a waste collection unit, typically in, but not limited to, a surgical environment. The smoke extraction system and the waste collection unit are connected to supply the medical waste collected thereby to a waste treatment (e.g. decontamination and/or sterilization) and disposal system. In such systems, the waste collection unit can be provided as a cart-mounted apparatus to provide mobility. The waste collection unit can then dock to known docking stations to dispose of the medical waste collected by the unit. As a result, surgical teams can quickly, easily, and efficiently maintain the integrity of a surgical site with a minimum of operating components.

Disposable manifold and filter assemblies are used to facilitate the collection of the medical waste into the waste collection unit. Typically, the manifold and filter assembly includes at least one filter to remove solid or semi-solid material such as bone chips, flesh, blood clots or the like from the medical waste generated by the surgical procedure or operation. The manifolds are disposed of between patients, or when the manifold is spent, i.e., filled with solid and semi-solid materials. An example of a disposable manifold for use in waste collection units is described in U.S. Pat. No. 6,331,246 to Beckham et al.

The '246 patent discloses a manifold and filter assembly for use with a waste collection unit to filter medical waste generated during a medical process. The manifold and filter assembly includes a manifold housing, inlet ports, an outlet port, and a series of filters disposed between the inlet and outlet ports. The filters retain solid and semi-solid materials from a fluid carrier entering the manifold housing through the inlet ports. Check valves are placed on the inlet ports to establish unidirectional flow. Currently, once the filters are plugged with debris, the manifold housing begins to fill with the medical waste. The check valves ensure that the medical waste does not reverse flow into the inlet ports. However, there is a need in the art for a manifold and filter assembly that includes a bypass to prevent the medical waste from reaching the inlet ports.

BRIEF SUMMARY OF THE INVENTION

The present invention provides a method of collecting medical waste in a waste collection unit using a disposable manifold and filter assembly. The disposable manifold and filter assembly includes a manifold housing having a bottom wall and a peripheral wall. The manifold housing defines a chamber and at least one inlet for the medical waste to enter into the chamber. A neck is disposed on the bottom wall of the manifold housing and extends downwardly therefrom to define at least one outlet. A filter basket is mounted in the chamber between the at least one inlet and the at least one outlet. The filter basket has a basket bottom wall with a first plurality of openings and a basket peripheral wall with a second plurality of openings. The second plurality of openings are spaced a predetermined distance from the first plurality of openings. The basket bottom wall is spaced from the manifold bottom wall and the basket peripheral wall is spaced from the manifold peripheral wall to define a fluid bypass between the manifold housing and the filter basket.

The method of the present invention includes inserting the neck of the disposable manifold and filter assembly into a waste inlet of the waste collection unit to direct the medical waste passing through the disposable manifold and filter assembly into the waste collection unit. At least one tube is connected to the at least one inlet of the manifold housing to provide a path for the medical waste to travel from a target site to the disposable manifold and filter assembly. A vacuum drawn in the waste collection unit pulls the medical waste through the at least one tube and into the disposable manifold and filter assembly where the medical waste is processed in a plurality of stages.

The plurality of stages includes a first stage in which the medical waste is filtered through the first plurality of openings in the basket bottom wall until the basket bottom wall becomes plugged with filtered-out material and the medical waste rises the predetermined distance to the second plurality of openings. The plurality of stages further includes a second stage, following the first stage, in which the medical waste is filtered through the second plurality of openings in the basket peripheral wall until the basket peripheral wall becomes plugged with filtered-out material and the medical waste rises to the fluid bypass. The plurality of stages includes a third stage, following the second stage, in which the medical waste enters the fluid bypass to bypass around the filter basket.

By providing this staged filtering/processing, life of the disposable manifold and filter assembly of the present invention can be prolonged. In particular, the third bypass stage allows the medical waste to flow around the filter basket once the filter basket is spent.

BRIEF DESCRIPTION OF THE SEVERAL VIEWS OF THE DRAWINGS

Advantages of the present invention will be readily appreciated as the same becomes better understood by reference to the following detailed description when considered in connection with the accompanying drawings wherein.

DETAILED DESCRIPTION OF THE INVENTION

Figure 18:
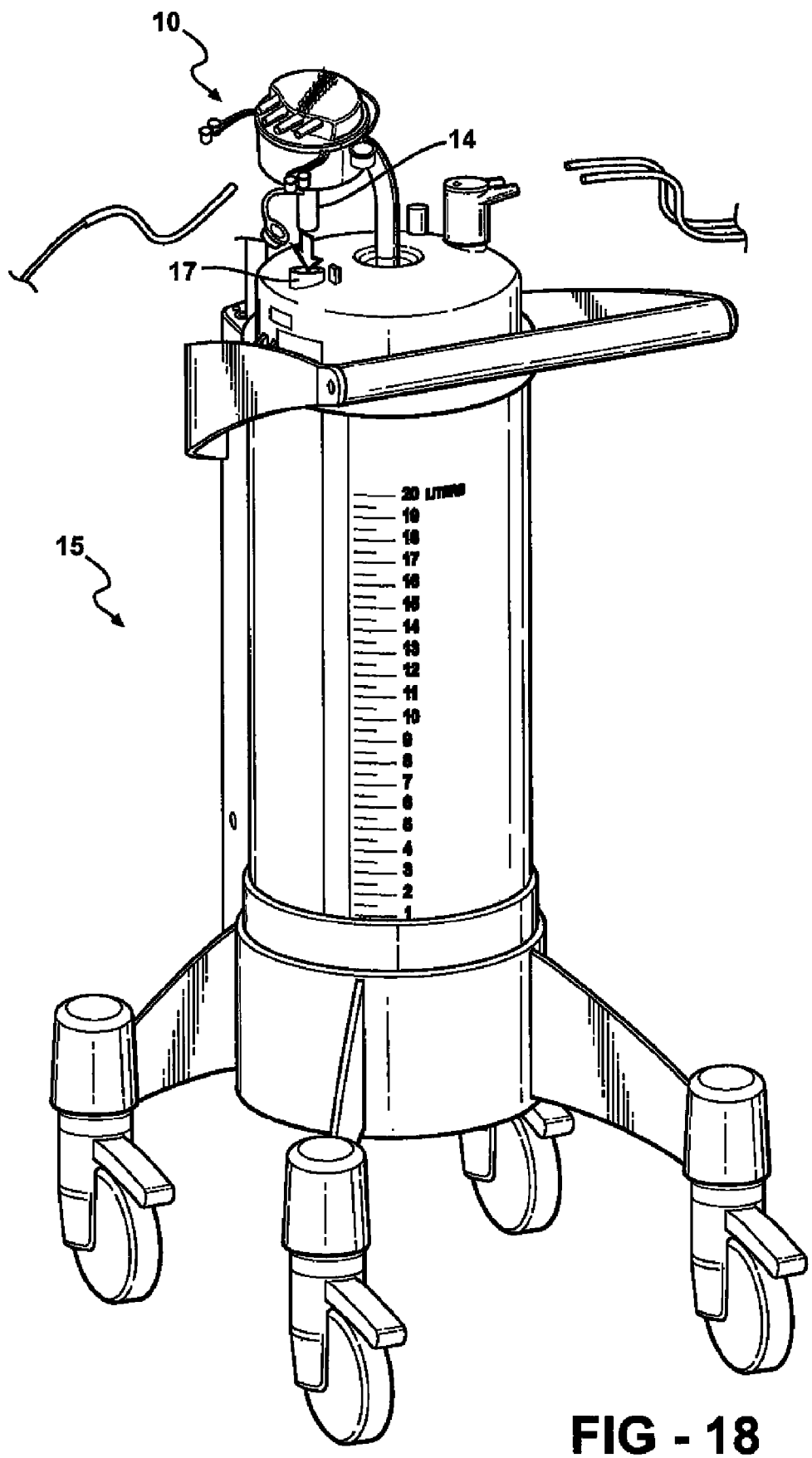
FIG. 18 is a perspective view of a waste collection unit in which the manifold and filter assemblies could be used.

Referring to the Figures, wherein like numerals indicate like or corresponding parts throughout the several views, a manifold and filter assembly of the present invention is generally shown at 10. The assembly 10 is intended for use with waste collection units to collect medical waste such as bodily fluids and materials from patients during medical procedures. Examples of waste collection units can be found in U.S. Pat. Nos. 5,997,733; 6,180,000; and 6,222,283, all incorporated herein by reference. Another example of a waste collection unit is shown at 15 in FIG. 18.

Figure 1:
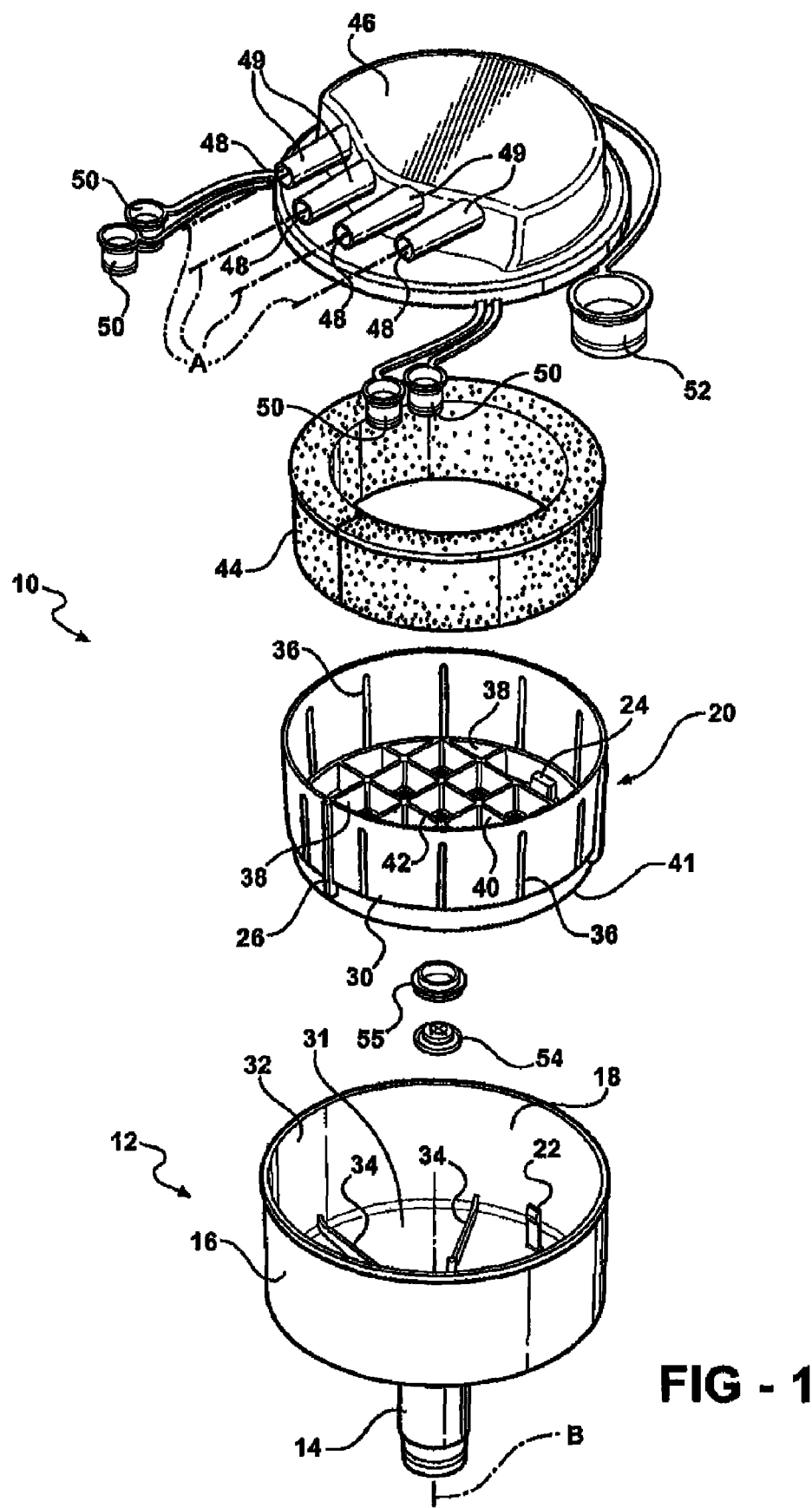
FIGS. 1 and 2 are exploded views of the manifold and filter assembly of the present invention.
Figure 2:
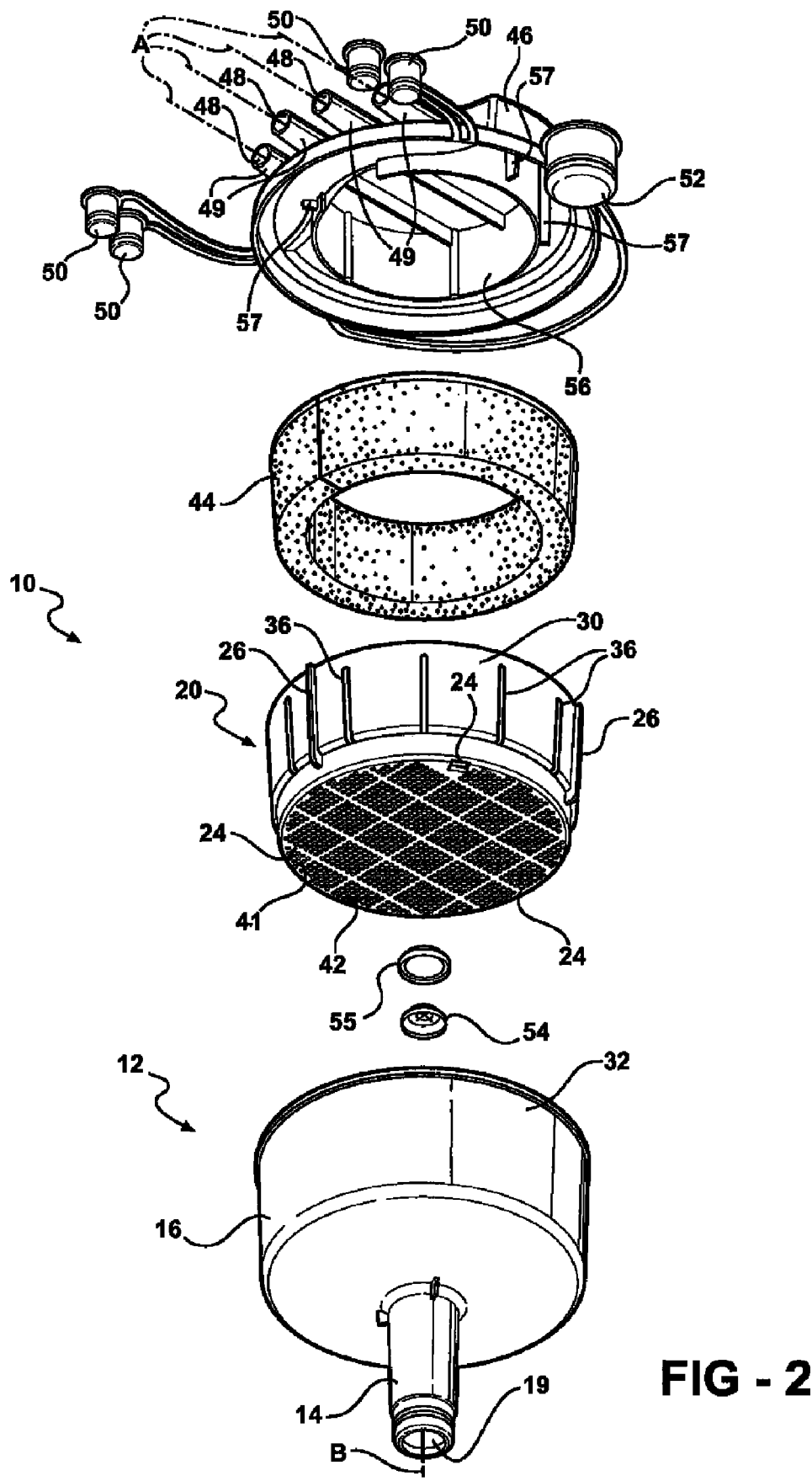

Referring to FIGS. 1 and 2, the assembly 10 has a base 12. The base 12 includes a cup-shaped manifold body 16 and a neck 14 (outlet tube 14) extending downwardly from the manifold body 16 to define an outlet 19. The neck 14 is adapted to be inserted into an inlet of a waste collection unit, such as the inlet 17 of the waste collection unit 15 shown in FIG. 18. The manifold body 16 defines a chamber 18. The chamber 18 is shown as being generally circular, but it should be understood by those of ordinary skill in the art that numerous other shapes could be used as effectively, for example, oval, square, rectangular, triangular, etc. The manifold body 16 has a bottom 31 and a peripheral wall 32 extending upwardly from the bottom 31 to define the chamber 18.

A filter basket 20 is adapted to fit within the chamber 18 of the manifold body 16. The filter basket 20 includes a bottom 41 and a peripheral wall 30 extending upwardly from the bottom 41. In the disclosed embodiment, a locking tab 22 is disposed on the bottom 31 of the manifold body 16 and extends upwardly therefrom. The locking tab 22 is adapted to snap-lock into a locking member 24 on the bottom 41 of the filter basket 20. As should be appreciated, there could be more than one locking tab 22 and locking member 24 if desired. In the disclosed embodiment there are three of each spaced approximately one hundred and twenty degrees relative to a center of the manifold body 16. Further, other types of locking methods could be employed to lock the filter basket 20 in the chamber 18, such as, for example, threaded connections, other connectors, welding, etc.

Spacers 26 are provided on the peripheral wall 30 of the filter basket 20. The spacers 26 engage the peripheral wall 32 of the manifold body 16 in order to provide a fluid bypass 28 between the peripheral wall 30 of the filter basket 20 and the peripheral wall 32 of the manifold body 16. The fluid bypass 28 can be seen for example in FIG. 4. The spacers 26 also provide the filter basket 20 with a semi-rigid configuration to support the filter basket 20 in the chamber 18.

In the disclosed embodiment, the manifold body 16 includes risers 34 disposed on the bottom 31 of the manifold body 16 and extending from the bottom 31 into the chamber 18. These risers 34 provide further support for the filter basket 20 and space the filter basket 20 from the bottom 31 of the manifold body 16 (see FIG. 5).

The filter basket 20 also includes a plurality of openings in fluid communication with the fluid bypass 28. The plurality of openings are further defined as a first plurality of perforations or holes 42 defined in the bottom 41 of the filter basket 20 and a second plurality of perforations 36, preferably vertical slots 36, defined in the peripheral wall 30 of the filter basket 20. The slots 36 provide fluid communication between an interior of the filter basket 20 and the fluid bypass 28. The bottom 41 of the filter basket 20 has a number of compartments 38 which are defined by a plurality of interior walls 40, preferably in a grid. A portion of the holes 42 are defined in a bottom of each of the compartments 38. These compartments 38 are illustrated in a waffle-like pattern, however, other patterns could be used, for example, circles, triangles, rectangles, etc. Referring particularly to FIG. 2, the holes 42 define a filtering screen. This screen filters the medical waste between the interior of the filter basket 20 and the space formed between the filter basket 20 and the bottom 31 of the manifold body 16.

A porous filter element 44 having a predetermined height is disposed within the filter basket 20. The filter element 44 allows the medical waste which enters the filter basket 20 to be filtered and then passed through the slots 36 into the fluid bypass 28. As shown, the filter element 44 is annular in shape. The filter element 44 is supported about and extends upwardly along the peripheral wall 30 of the filter basket 20 thereby requiring the medical waste to pass through the filter element 44 to reach the slots 36. The filter element 44 retains filtered-out material, e.g., debris, in the interior of the filter basket 20 such that debris slowly builds upward along the predetermined height of the filter element 44 to maximize a filtering capacity of the filter element 44 and the filter basket 20. Both the filter basket 20 and the filter element 44 act as filtering members, however, the filter basket 20 is preferably more rigid than the filter element 44.

A manifold cap 46 closes the manifold body 16. The manifold cap 46 includes a plurality of inlets 48. Each of the inlets 48 includes an entrance tube 49 disposed about an entry axis A. The entrance tubes 49 are disposed above the fluid bypass 28 such that the medical waste can enter the fluid bypass 28 without flowing back through the inlets 48. Preferably, all of the entry axes A are parallel. The outlet 19 extends downwardly from the bottom 31 of the manifold body 16 about an outlet axis B approximately normal to said entry axes A.

The inlets 48 are adapted to be connected to tubes which extend to, for example, a patient undergoing surgery. The waste collection unit, such as the waste collection unit 15 of FIG. 18, typically has a vacuum source (not shown) which pulls a vacuum through the assembly 10 and the tubes to draw the medical waste from the patient into the assembly 10. As shown, there are four inlets 48, but there could be as little as one and as many as desired. With the four inlets 48 shown, in the event less than four inlets 48 are used, inlet port caps 50 are provided to close off the inlets 48 that are not being used.

In addition, the inlet port caps 50 can be used to close off the inlets 48 during transportation. An outlet port cap 52 is shown for closing the neck 14 during transportation. As shown, integrally formed connection straps extend from the caps 50, 52 to the manifold cap 46.

Referring specifically to FIG. 2, an underside of the manifold cap 46 has a splash wall 56 which is configured to absorb fluid energy from the medical waste entering the assembly 10 from the inlets 48 by deflecting the medical waste as it enters the assembly 10 from the inlets 48 toward the filter basket 20. To this end, the splash wall 56 is oriented normal to the entry axes A. The splash wall 56 guides the accumulation of the debris in such a way as to prolong the life of the assembly 10. The splash wall 56 also contains features such as tabs 57 that serve to hold the filter element 44 in place.

Figure 3:
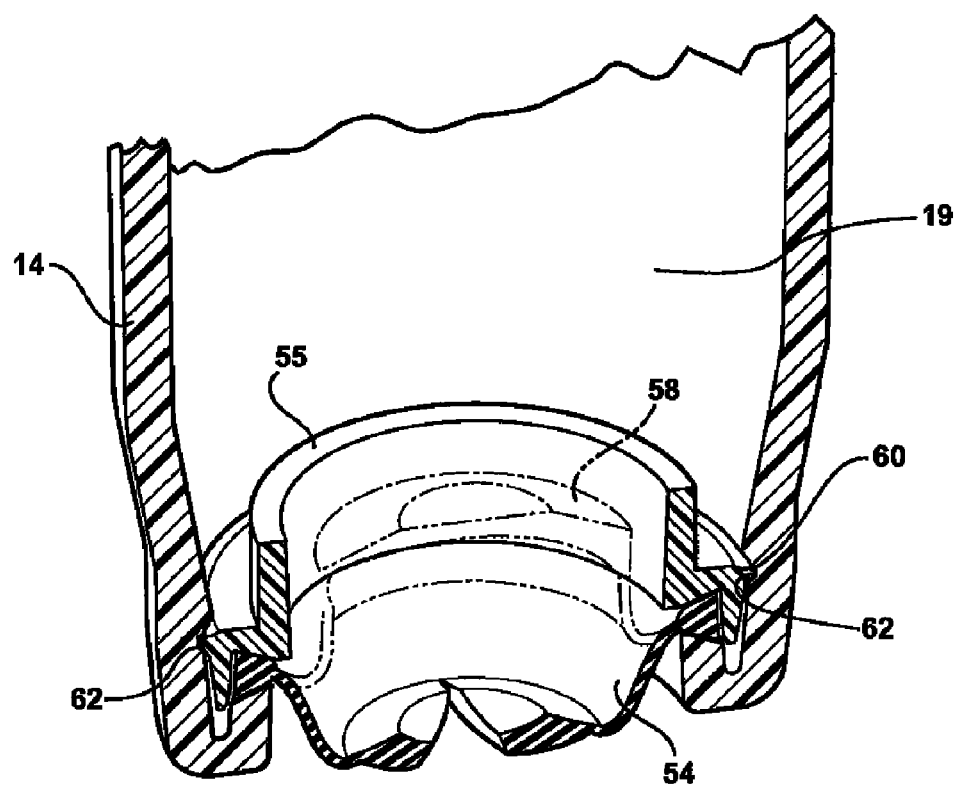
FIG. 3 is a cross-sectional view of an outlet of the manifold and filter assembly illustrating a check valve disposed therein.

Referring to FIG. 3, a waste retention valve 54, preferably a check valve 54, is illustrated which fits within the neck 14 to contain any medical waste which may be in the assembly 10 during transportation or disposal. The check valve 54 is configured so that it will move to an open position when a predetermined pressure is applied thereto, e.g., when a predetermined vacuum is pulled within the assembly 10. The check valve 54 is normally in a closed position and will automatically close when the vacuum is discontinued. In FIG. 3, the check valve 54 is shown in the open position as a result of the vacuum pulling the check valve 54 from the closed position shown in dotted lines 58. A locking ring 55 is shown locking the check valve 54 in place. As shown, the locking ring 55 has an annular flange 60 which locks into a groove 62 formed in the neck 14.

Figure 4:
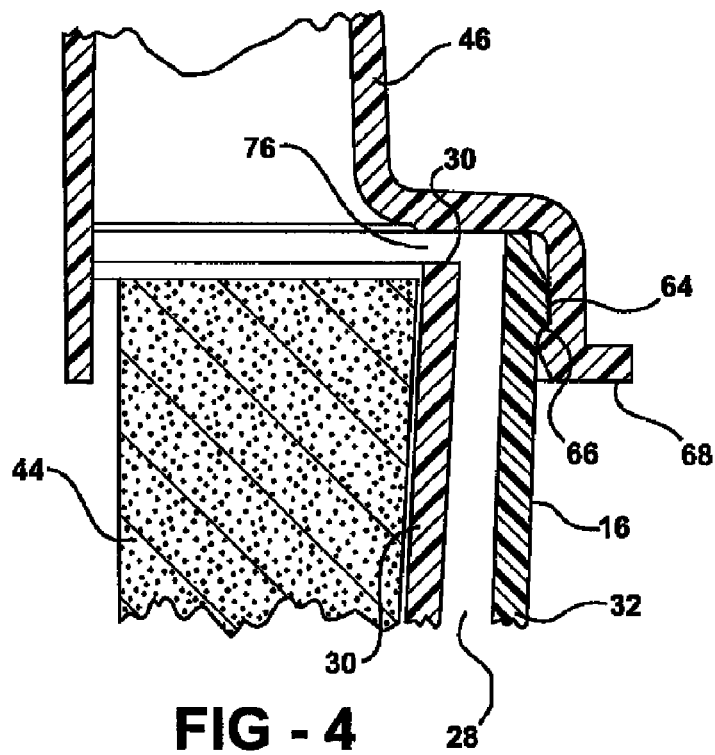
FIG. 4 is a cross-sectional view illustrating a snap-fit connection between a manifold cap and manifold body of the manifold and filter assembly.

Referring to FIG. 4, the manifold cap 46 is shown snap-fit to the manifold body 16. As shown, the manifold body 16 has an outer rim 64 which is received by a mating inner rim 66 on the manifold cap 46. In this way, a tab 68 can be raised to disengage the mating rims 64 and 66 to remove the manifold cap 46, if desired.

In the disclosed embodiment, the base 12, filter basket 20 and manifold cap 46 are all made of plastic material, more preferably thermoplastic material, and are intended to be single-use items and disposed after each operation. The filter element 44 is made of filtering material such as plastic, steel wool, etc., and is also intended to be disposable. At least portions of the base 12, filter basket 20, and manifold cap 46 are made from a semi-transparent material. This allows a user to see into the chamber 18 and determine whether the assembly 10 requires disposal.

Figure 5:
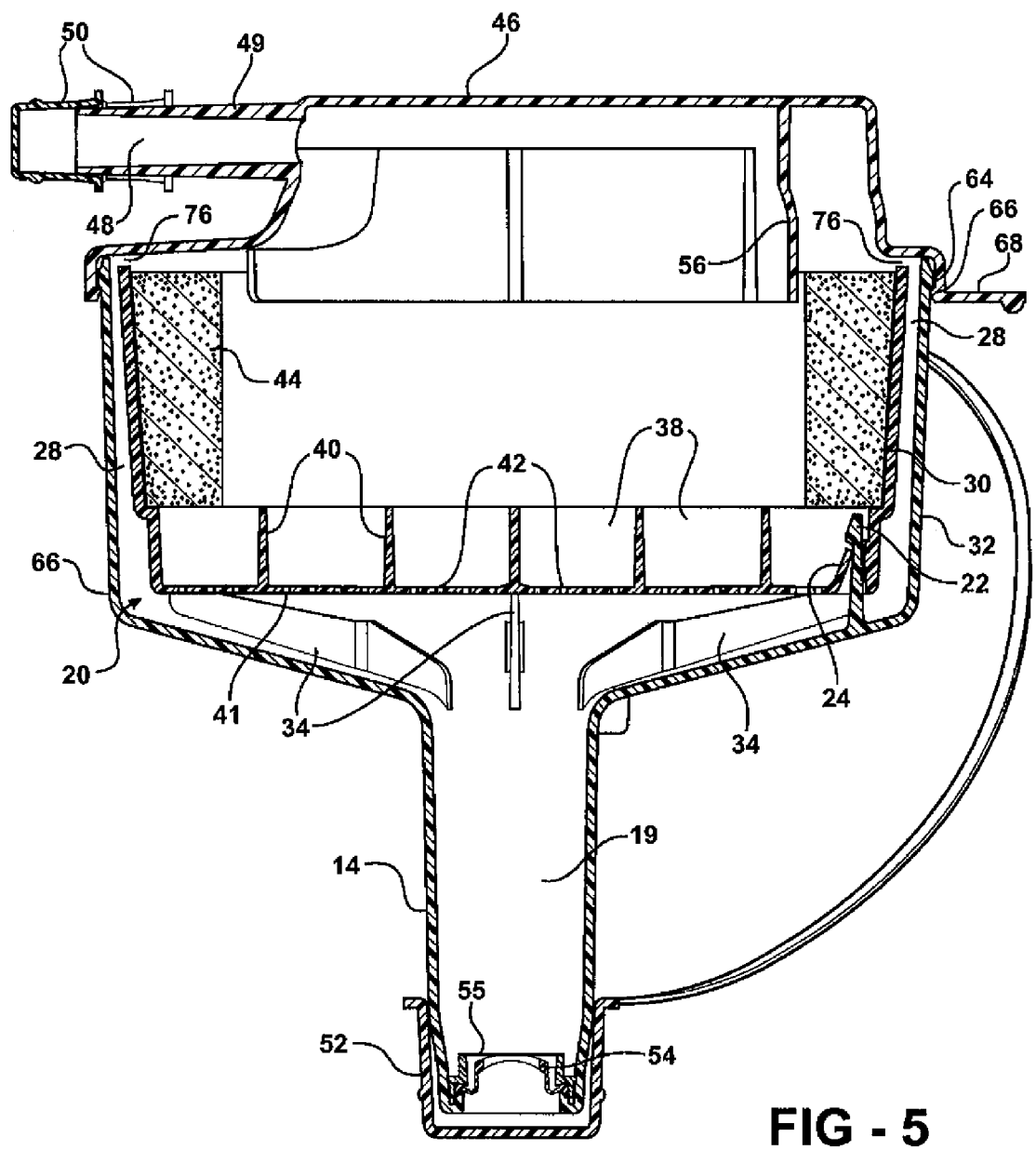
FIG. 5 is a cross-sectional view of the manifold and filter assembly.
Figure 6:
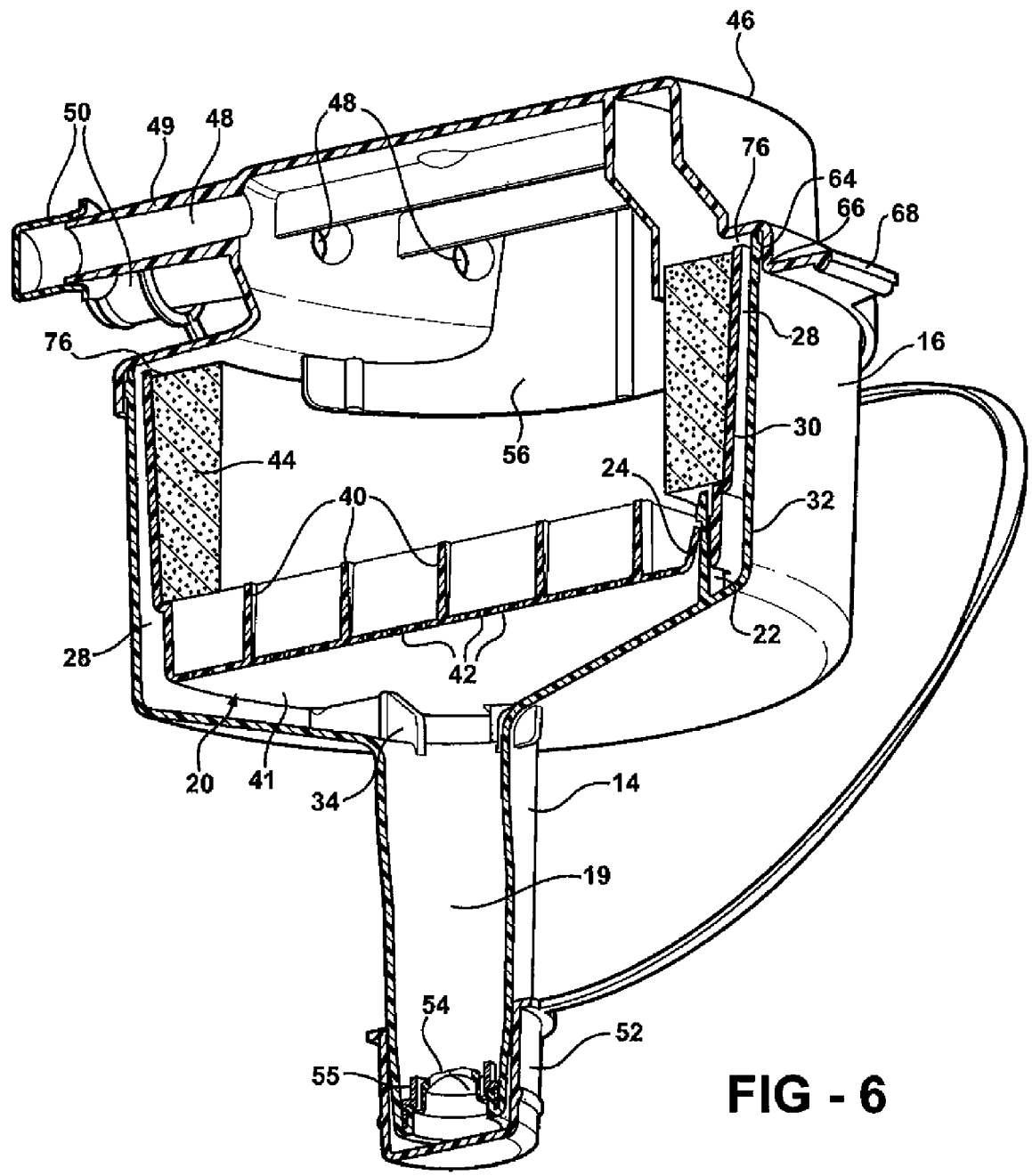
FIGS. 6 and 7 are cross-sectional perspective views of the manifold and filter assembly.
Figure 7:
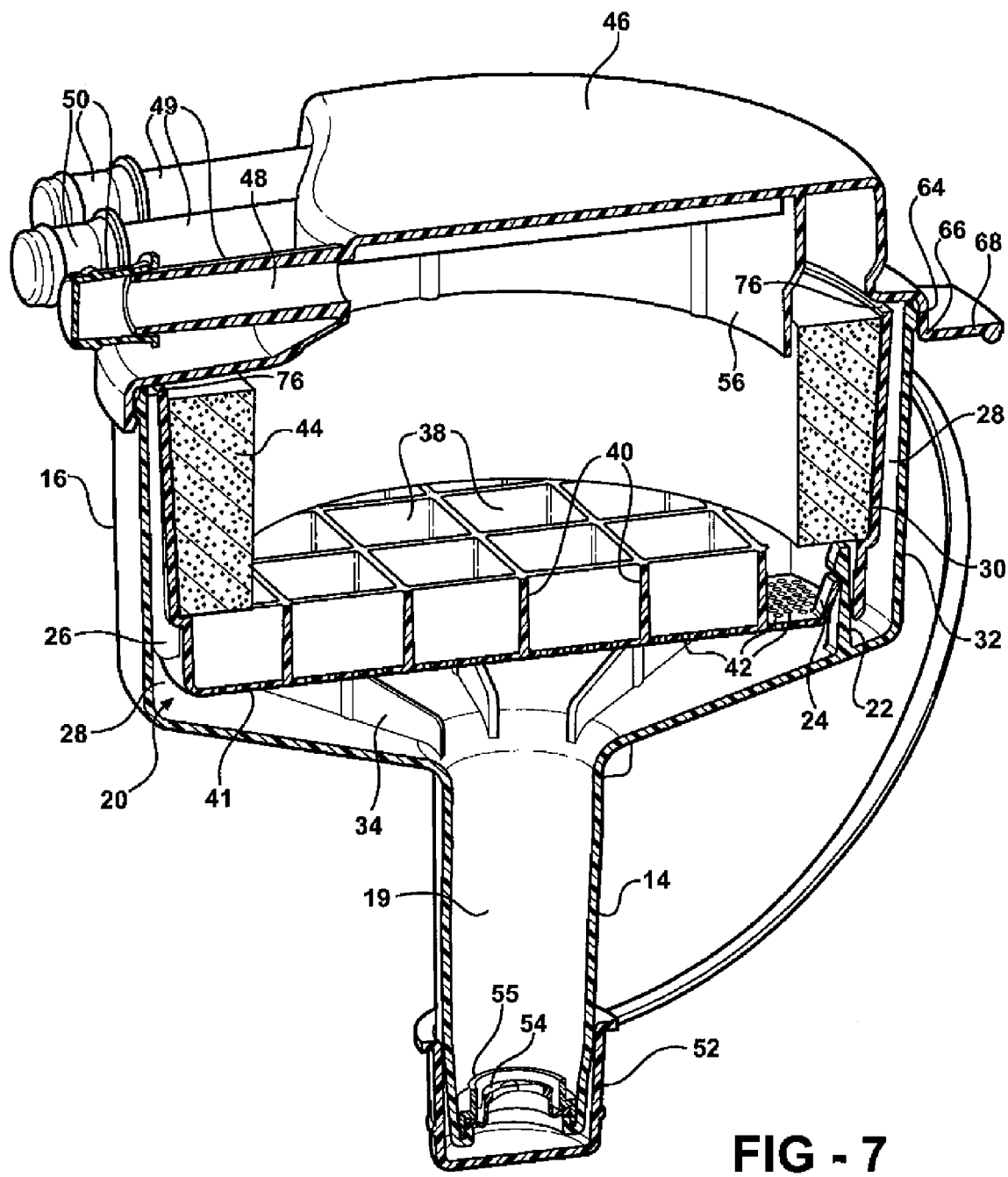

FIGS. 5-7 are cross-sectional views of the assembly 10 showing the various components described above.

Referring to FIGS. 8-12, operation of the assembly 10 will be described. As will be appreciated by those of ordinary skill in the art, the assembly 10 is inserted into the inlet 17 of the waste collection unit 15. The waste collection unit 15 has a vacuum source that draws a vacuum in the waste collection unit 15 thereby drawing the medical waste from the patient, e.g., from a surgical site, through tubes 72 connected to the inlets 48. The medical waste is illustrated by numeral 74.

Figure 8:
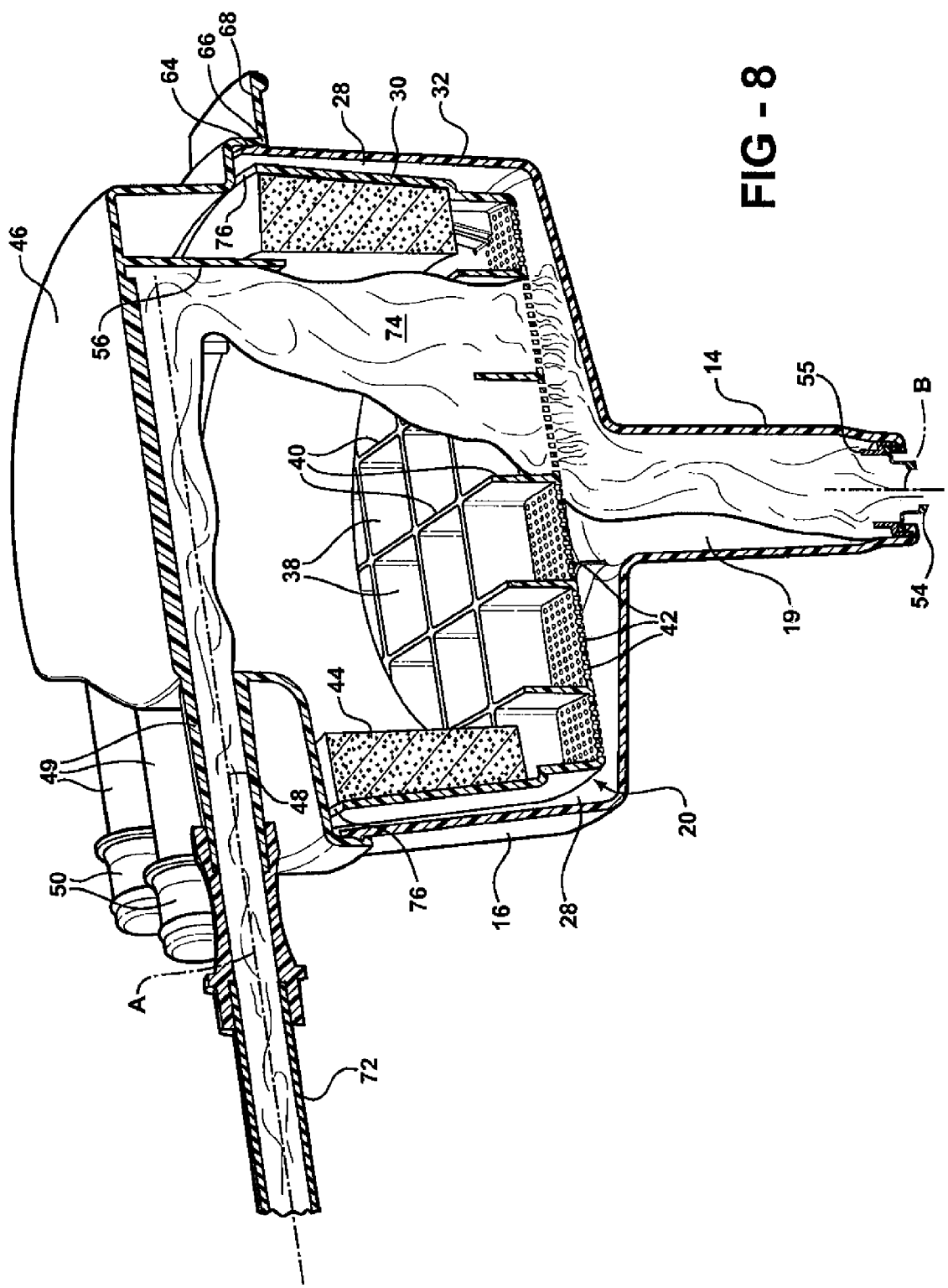
FIGS. 8-11 are cross-sectional perspective views of the manifold and filter assembly illustrating various stages of use.

Referring to FIG. 8, the medical waste 74 enters the assembly 10 through at least one of the inlets 48. A coupling is shown coupling the tube 72 to the inlet 48. Those of ordinary skill in the art will appreciated that numerous other couplings could be used to attach the tube 72 to the inlet 48. In fact, the tube 72 could be directly attached at the inlet 48. As illustrated, caps 50 are shown closing the additional inlets 48 which are not being used in this illustration.

The medical waste 74 is drawn into the assembly 10 and engages the splash wall 56. There, the medical waste 74 is deflected downwardly into the filter basket 20. The medical waste 74 begins to collect in one of the compartments 38 and is filtered by the holes 42 in the respective compartments 38. The medical waste 74 then enters the space between the bottom 31 of the manifold body 16 and the filter basket 20 and is pulled, by vacuum, into the outlet 19. As illustrated, the check valve 54 is drawn downwardly to the open position to allow the filtered medical waste to enter a collection area of the waste collection unit 15. The holes 42 screen any debris, e.g., solid or semi-solid materials such as bone chips, flesh, blood clots, or the like, from the medical waste 74 that may otherwise be drawn into the assembly 10, so that they do not enter the outlet 19, and subsequently the waste collection unit 15.

Figure 9:
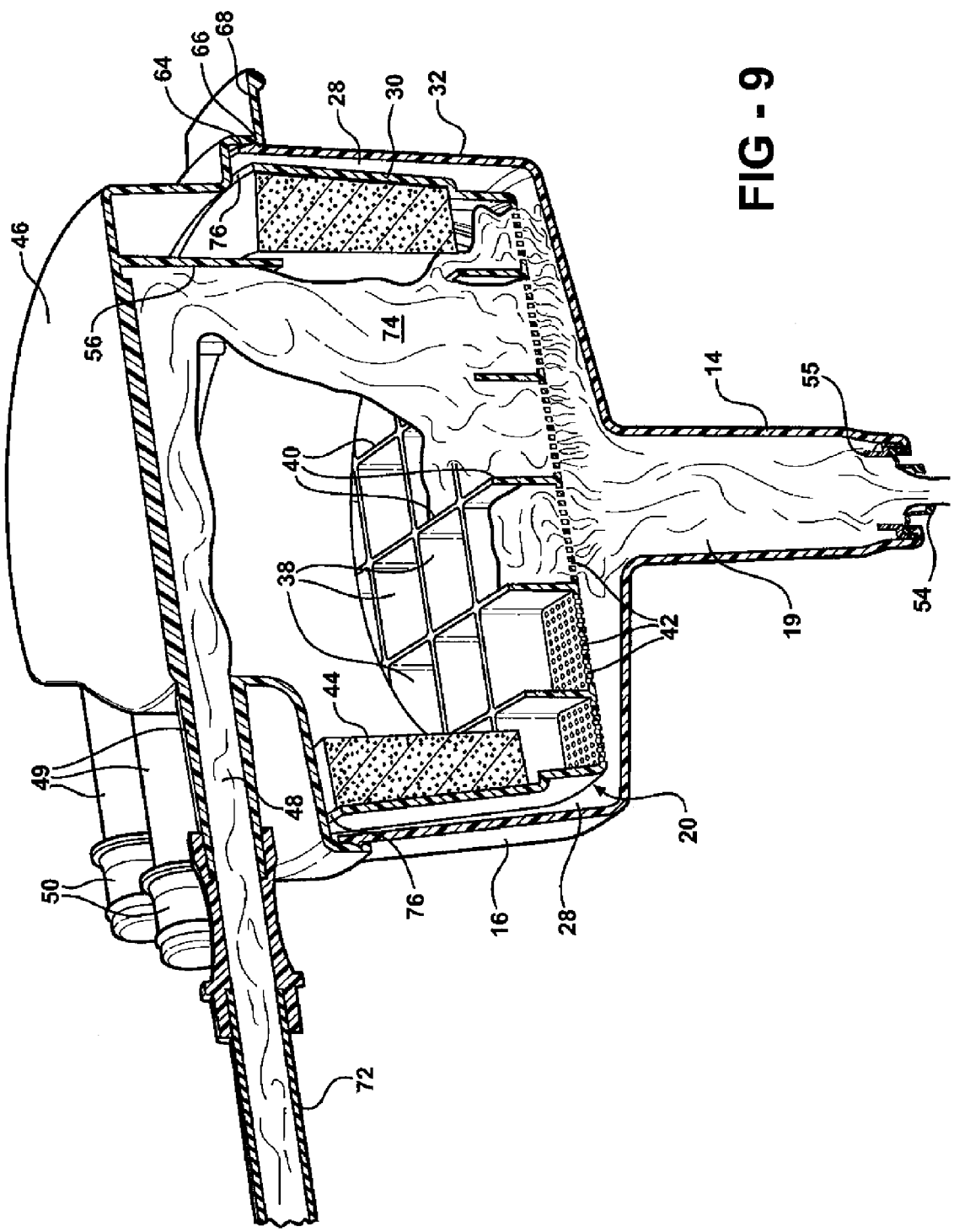

Referring to FIG. 9, the medical waste 74, which is entering the assembly 10, is compartmentalized within the compartments 38 allowing the other compartments 38 to remain open and free of the medical waste 74. This allows the vacuum which is being pulled to continue to draw the medical waste into the assembly 10. In the event any one or more of the compartments 38 becomes clogged with debris and/or fluid, the other compartments 38 are still open and continue to allow sufficient vacuum for operation of the assembly 10. Here, the compartments 38 are becoming full. However, additional compartments 38 remain open allowing the vacuum to continue to be drawn through the assembly 10.

Figure 10:
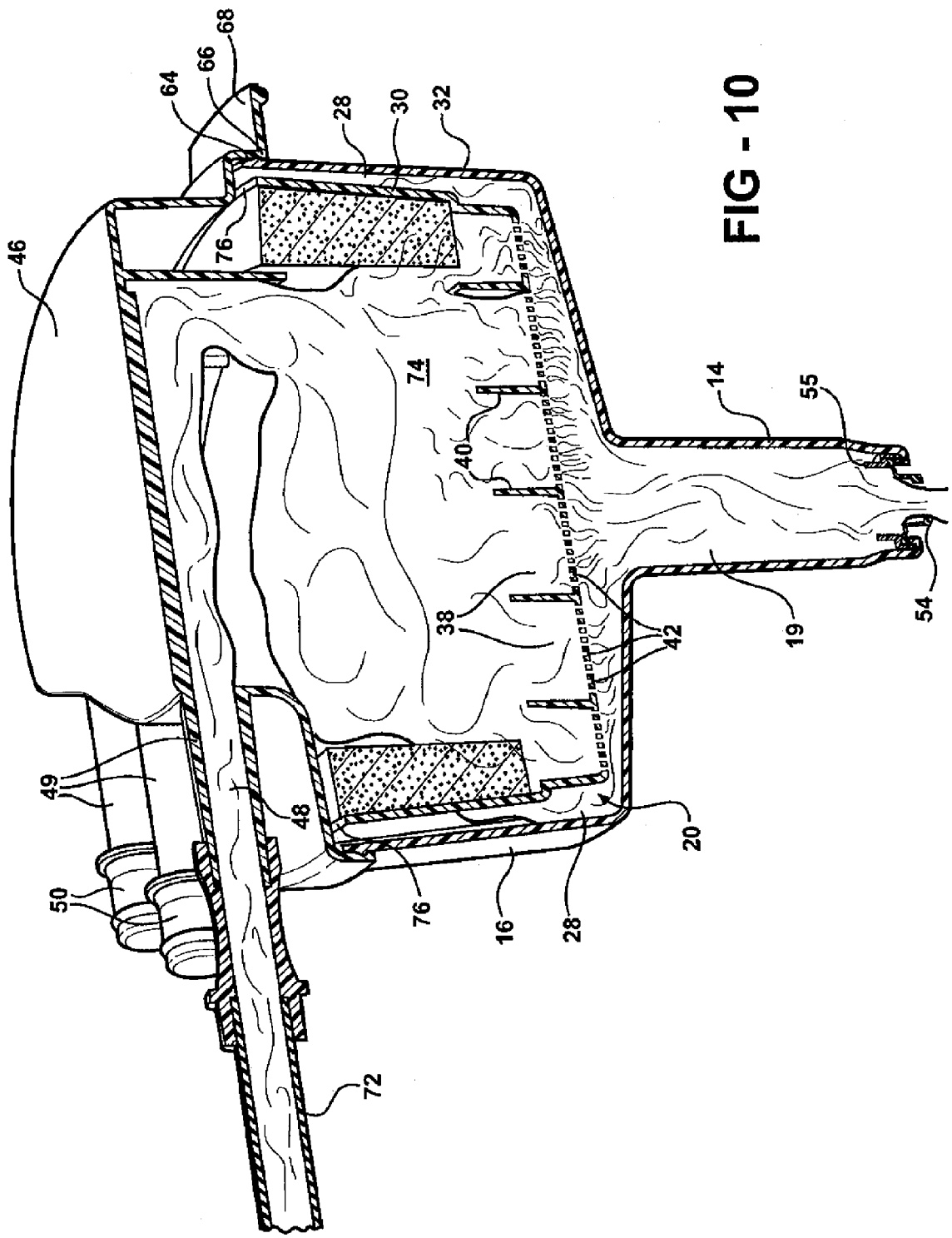

Referring to FIG. 10, the compartments 38 have become clogged and filled with debris and fluid. However, the vacuum is still able to be pulled through the assembly 10 through the filter element 44 and the slots 36. Now, the filter element 44 acts to filter out the debris from the medical waste 74. Thus, filtered medical waste 74 is now drawn into the fluid bypass 28 formed between the peripheral wall 30 of the filter basket 20 and the peripheral wall 32 of the manifold body 16.

Figure 11:
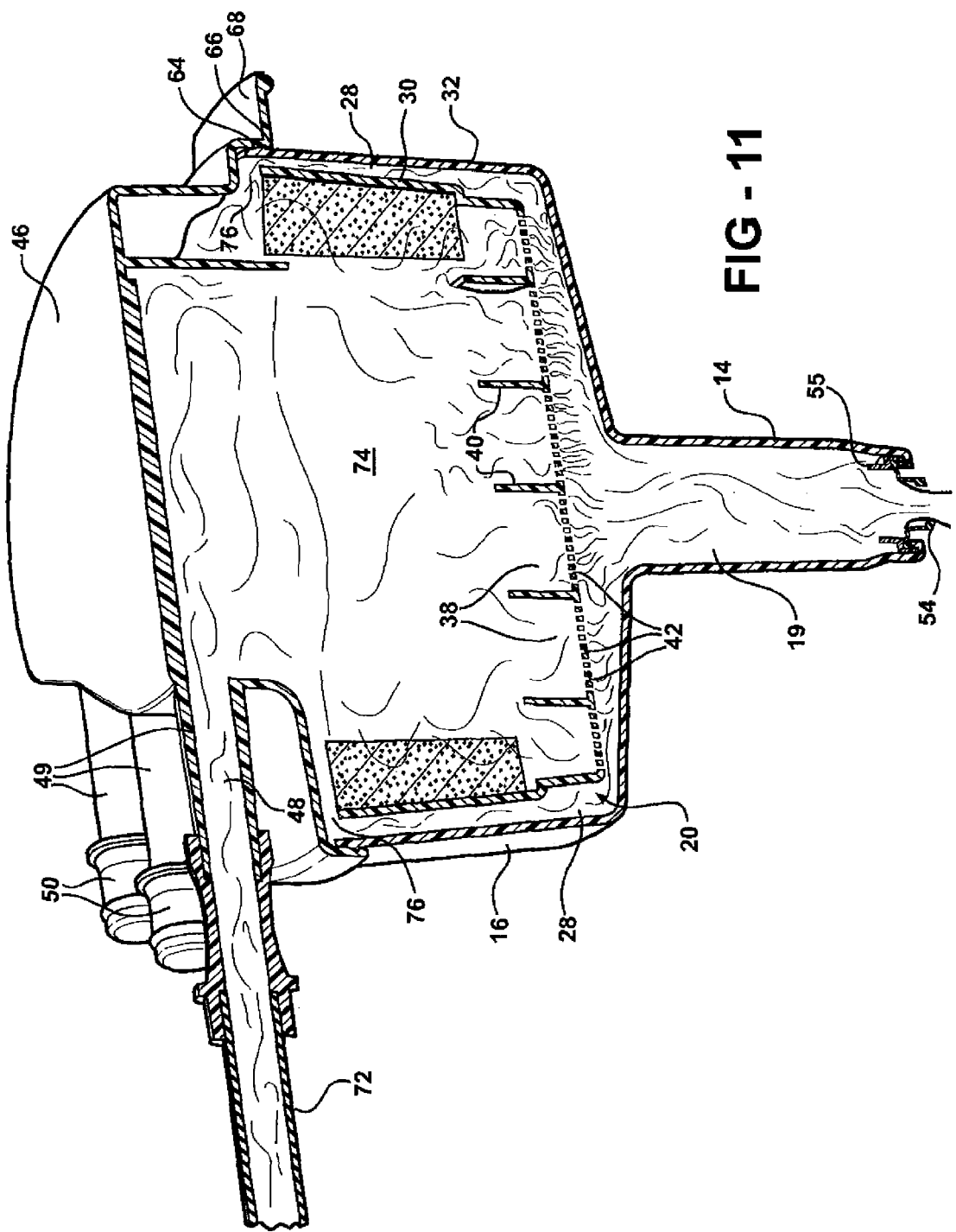

Finally, referring to FIG. 11, the filter basket 20 is spent and unable to further filter the medical waste 74. The medical waste 74 is now to the point that it has filled the filter basket 20. At this point, the medical waste 74 flows over top of the filter element 44 and the peripheral wall 30 of the filter basket 20 through a space 76 formed between the manifold cap 46 and a top of the filter element 44. The medical waste 74 flows from the space 76 into the fluid bypass 28 and then through the outlet 19. Due to this space 76, the assembly 10 will continue to allow the medical waste 74 to be pulled in through the inlets 48. In other words, the assembly 10 will not become filled to the point that no vacuum is pulled through the assembly 10. As a result, the space 76 ensures that the vacuum will continually be pulled even though the filter basket 20 has become completely filled with the medical waste 74. Additionally, the space 76 is small enough so that larger debris pulled into the assembly 10 will be blocked and prevented from entering the waste collection unit 15. This space 76, along with the fact that the inlets 48 are disposed above each of the space 76, the top of the filter element 44, and the top of the peripheral wall 30 of the filter basket 20, ensure that no cross-contamination between inlets 48 occurs.

Figure 12:
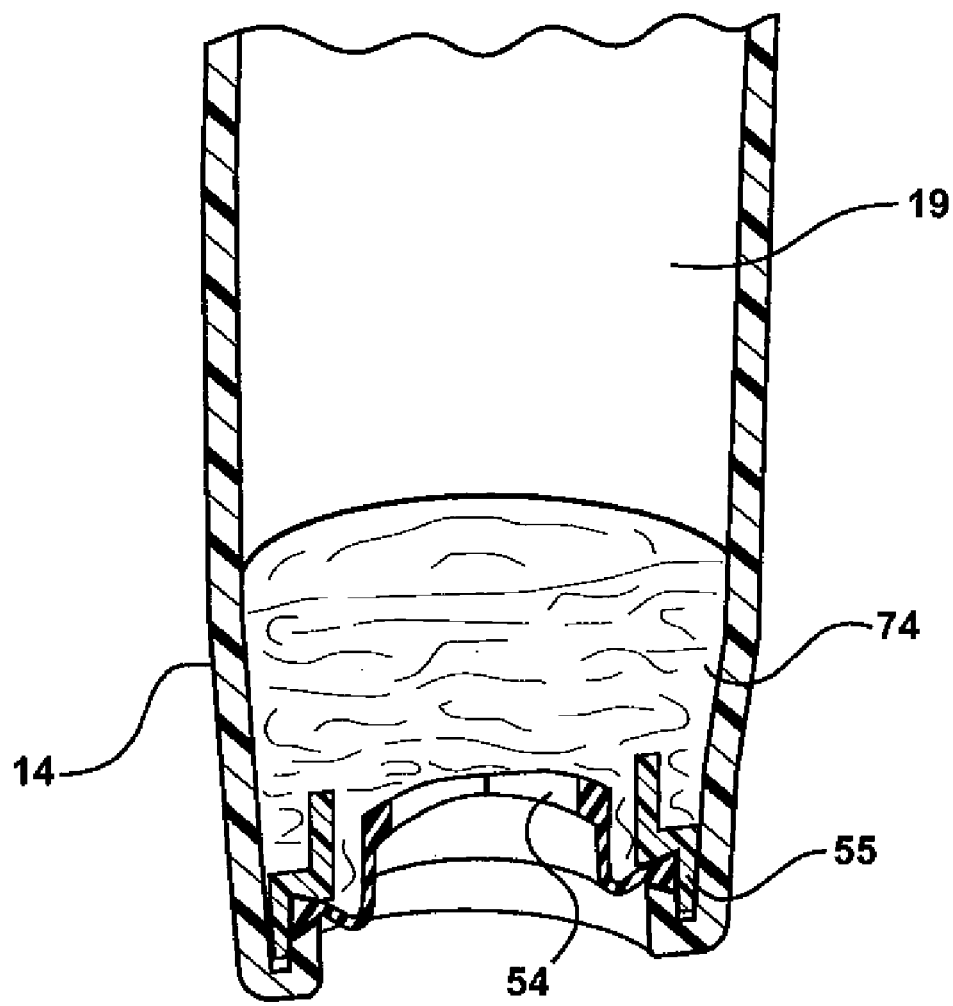
FIG. 12 is a cross-sectional perspective view of the outlet illustrating the check valve in a closed position.
Figure 13:
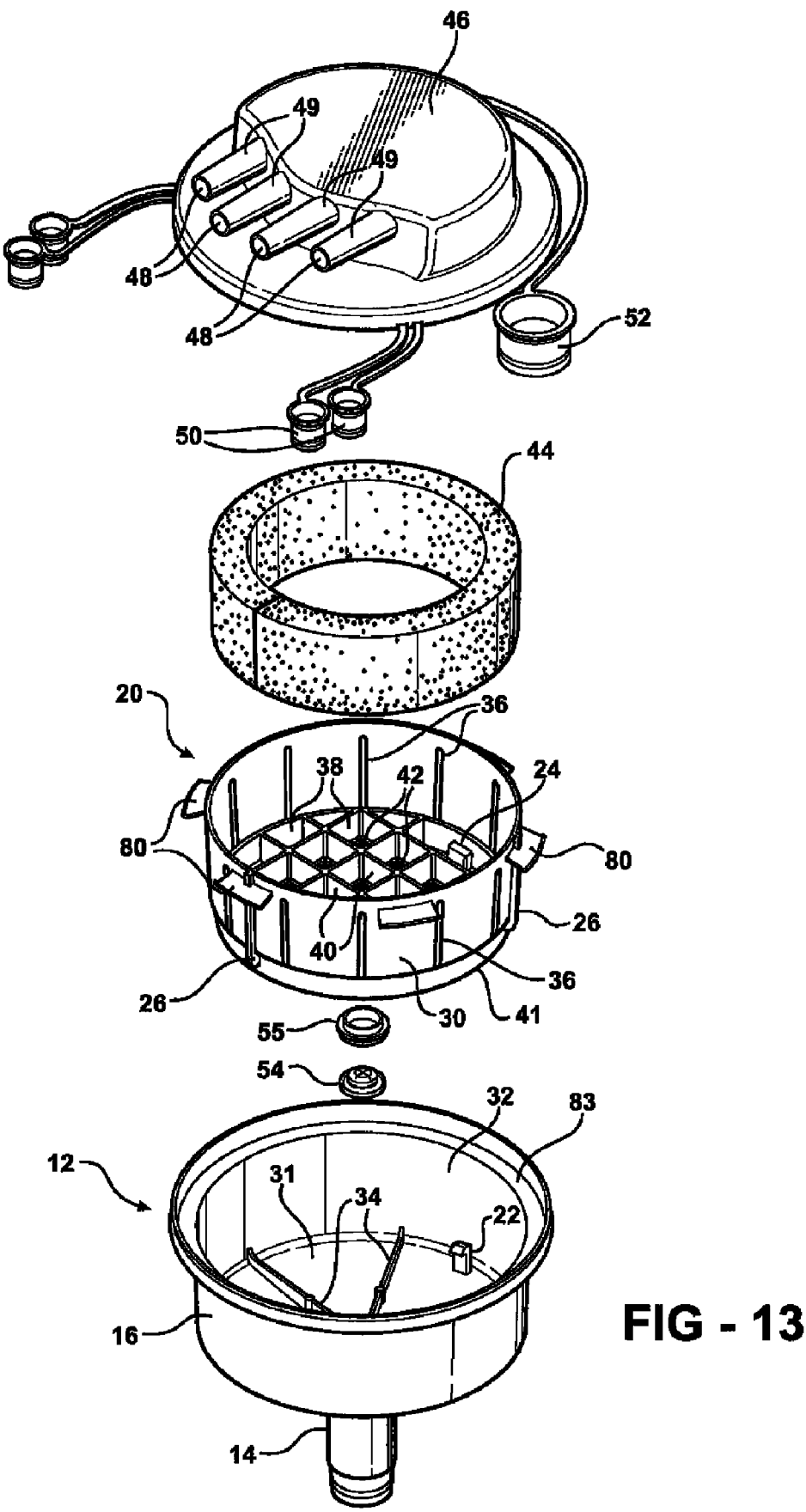
FIG. 13 is an exploded view of an alternative manifold and filter assembly of the present invention.

Referring to FIG. 12, the check valve 54 is shown when the vacuum has been stopped. The check valve 54 draws into its normally closed position within the outlet 19 of the neck 14 and also serves to seal the outlet 19. In this way, the assembly 10 can be removed from the waste collection unit 15 without the medical waste 74 leaking or dripping from the neck 14.

Referring to FIGS. 13-17, a further embodiment of the present invention is illustrated. In this embodiment, the same numbers will be used to indicate similar components. Generally, in this embodiment, the space 76 is controlled so that it is only opened when a load on the filter basket 20 exceeds a predetermined load or threshold, such as when the filter basket 20 is full of the medical waste 74, or when the vacuum results in a load on the filter basket 20 exceeding the predetermined load.

Figure 14:
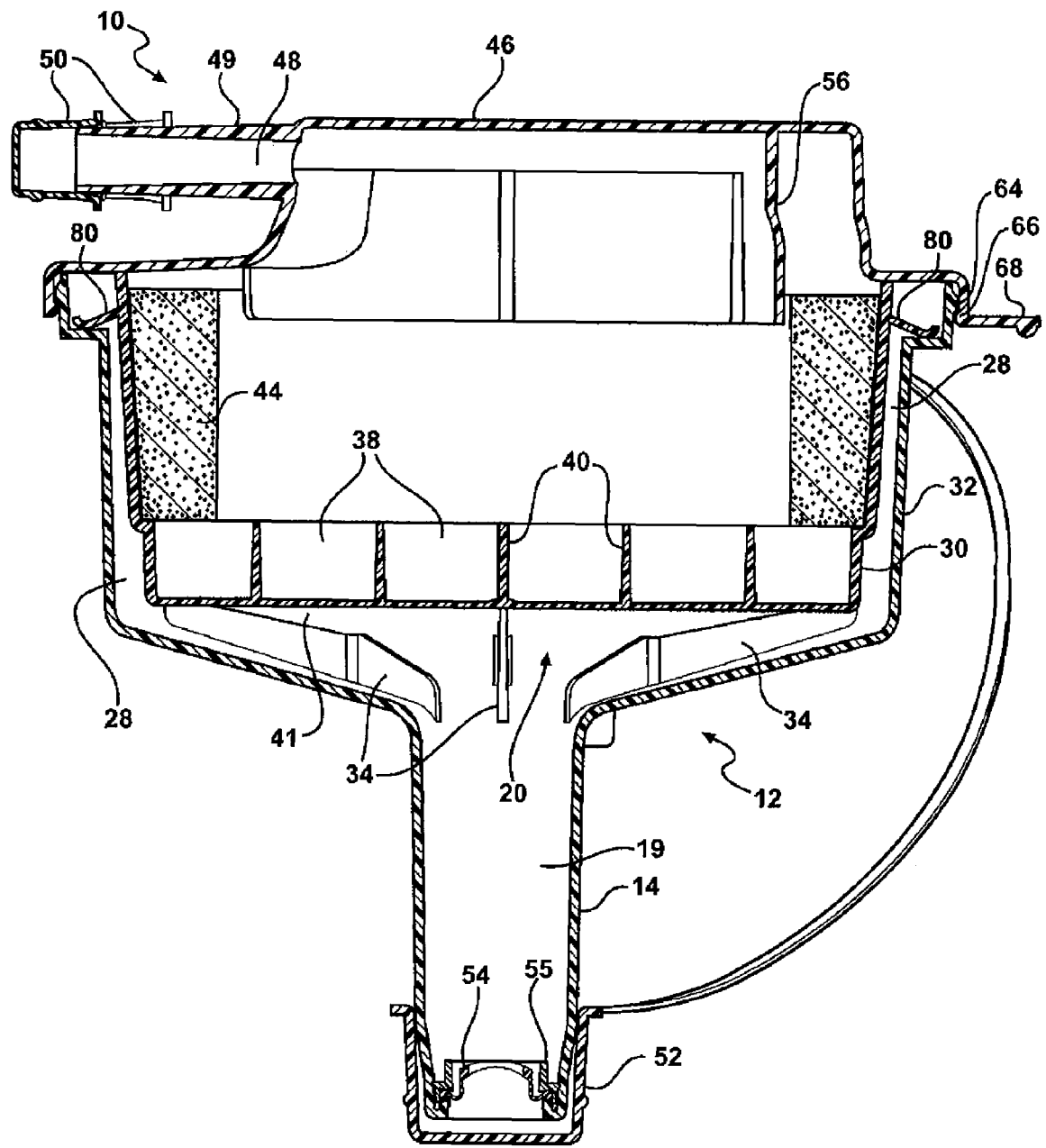
FIG. 14 is a cross-sectional view of the alternative manifold and filter assembly with a filter basket in a closed position.
Figure 15:
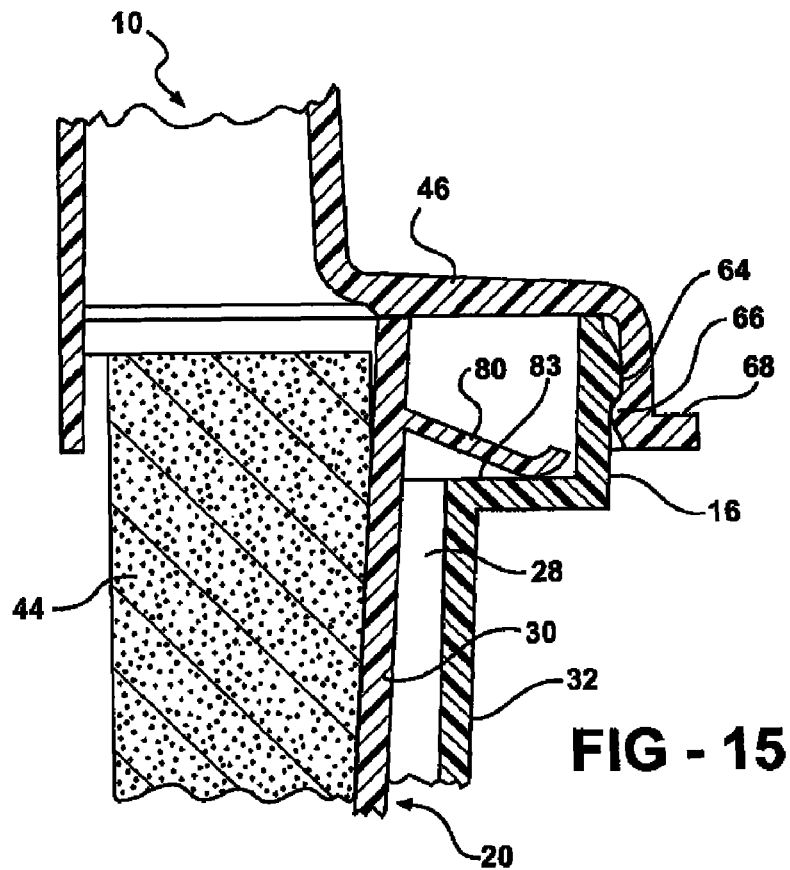
FIG. 15 is a blown-up view of a resilient tab of the filter basket holding the filter basket in the closed position.

Referring to FIGS. 14 and 15, there is no space 76 between the manifold cap 46 and the filter basket 20, i.e., the fluid bypass 28 is closed. Resilient members 80 in the form of flexible fingers or tabs 80 extend outwardly from the peripheral wall 30 of the filter basket 20 and rest on a shoulder 83 defined in the peripheral wall 32 of the manifold body 16. The flexible fingers 80 act as springs to springably bias the filter basket 20 upwardly so that filter basket 20 engages the manifold cap 46. It should be understood that any form of resilient member or biasing member would work, such as for example a leaf or coil spring.

Figure 17:
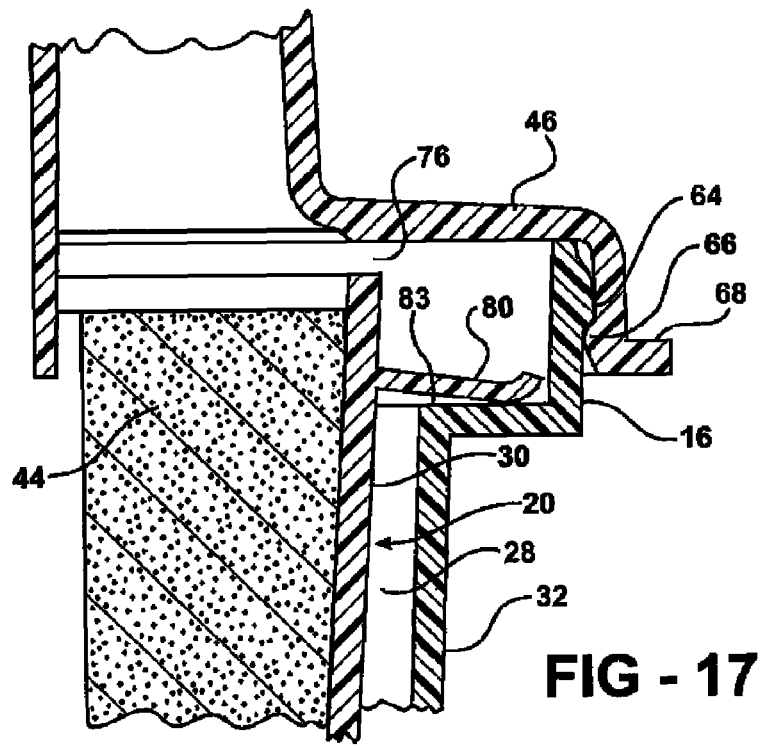
FIG. 17 is a blown-up view of the resilient tab of the filter basket flexing to place the filter basket in the open position.
Figure 16:
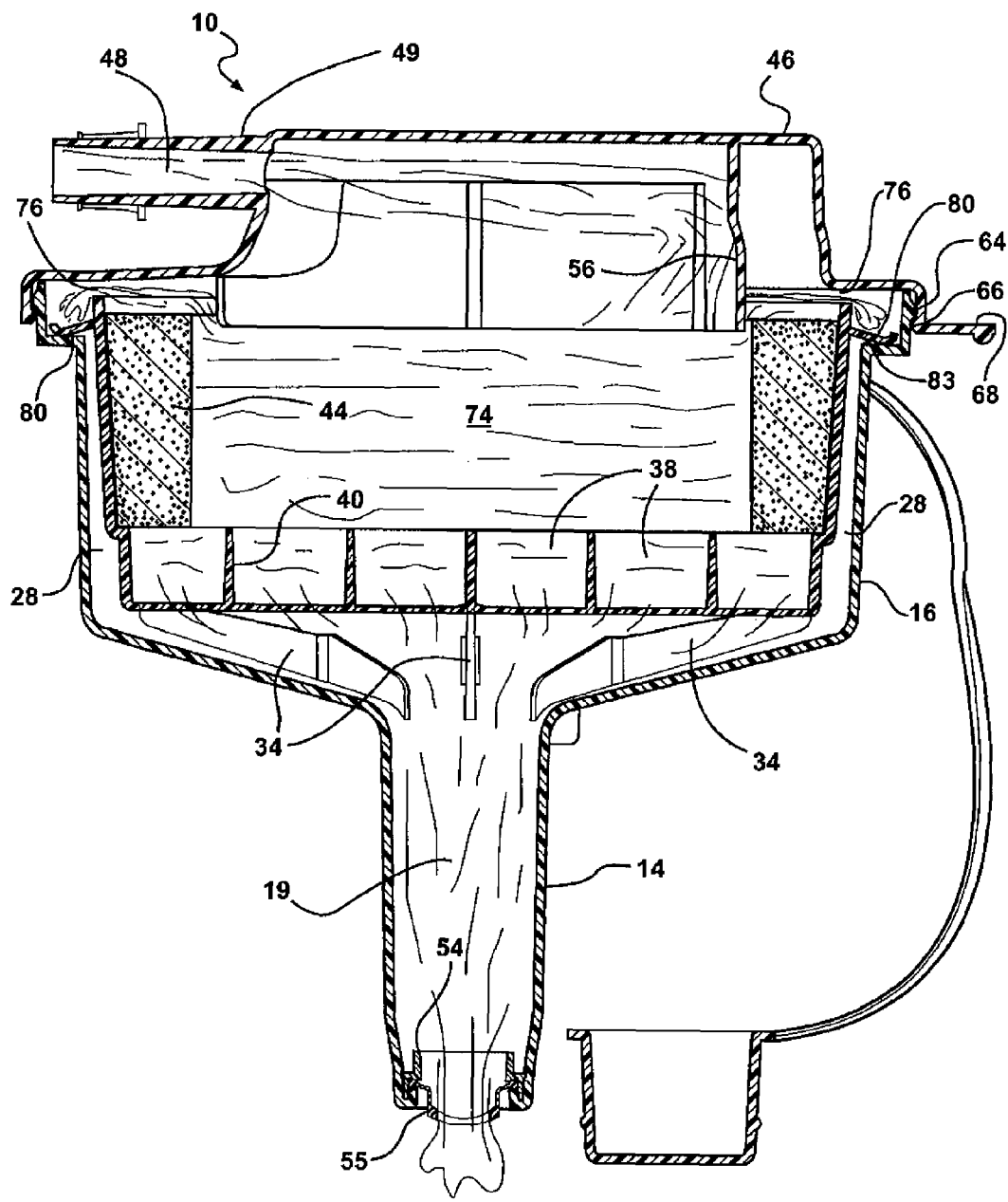
FIG. 16 is a cross-sectional view of the alternative manifold and filter assembly with the filter basket in an open position.

Referring to FIGS. 16-17, the flexible fingers 80 are shown in their flexed position creating the space 76 between the filter basket 20 and the manifold cap 46, i.e., the fluid bypass 28 is open. The flexible fingers 80 have been flexed because the filter basket 20 has become full and/or the vacuum has pulled the filter basket 20 downward exposing the space 76. As will be appreciated, the medical waste 74 can now flow through the space 76 into the fluid bypass 28 and ultimately through the outlet 19.

There has been shown and described a unique design and concept of a manifold and filter assembly. It is understood that those skilled in the art may conceive of modifications and/or variations to the specific embodiments shown and described herein. Any such modifications or variations which fall within the purview of this description are intended to be included herein as well. It is understood that the description herein is intended to be illustrative only and is not intended to be limited. Rather, the scope of the invention described herein is limited only by the claims appended hereto.

What is claimed is:

1. A method of collecting medical waste in a waste collection unit having a waste inlet for receiving the medical waste, said method comprising the steps of:
   providing a disposable manifold and filter assembly including:
      a manifold housing having a manifold bottom wall and a manifold peripheral wall, the manifold housing defining a chamber and at least one inlet;
      a neck disposed on the manifold bottom wall and extending downwardly therefrom to define at least one outlet; and
      a filter basket mounted in the chamber between the at least one inlet and the at least one outlet, the filter basket having a basket bottom wall with a first plurality of openings and a basket peripheral wall with a second plurality of openings spaced a predetermined distance from the first plurality of openings to define an imperforate wall section between the first and second plurality of openings, the basket bottom wall being spaced from the manifold bottom wall and the basket peripheral wall being spaced from the manifold peripheral wall to define a fluid bypass between the manifold housing and the filter basket;
   inserting the neck of the disposable manifold and filter assembly into the waste inlet of the waste collection unit to direct the medical waste passing through the disposable manifold and filter assembly into the waste collection unit;
   connecting at least one tube to the at least one inlet of the manifold housing to provide a path for the medical waste to travel from a target site to the disposable manifold and filter assembly; and
   drawing a vacuum in the waste collection unit to pull the medical waste through the at least one tube and into the disposable manifold and filter assembly where the medical waste is processed in a plurality of stages including a first stage in which the medical waste is filtered through the first plurality of openings in the basket bottom wall until the basket bottom wall becomes plugged with filtered-out material and the medical waste rises the predetermined distance defined by the imperforate wall section to the second plurality of openings, a second stage, following the first stage, in which the medical waste is filtered through the second plurality of openings in the basket peripheral wall until the basket peripheral wall becomes plugged with filtered-out material and the medical waste rises to the fluid bypass, and a third stage, following the second stage, in which the medical waste enters the fluid bypass to bypass the filter basket.

2. A method as set forth in claim 1 including connecting a plurality of tubes to a plurality of inlets on the manifold housing.

3. A method as set forth in claim 1 wherein the disposable manifold and filter assembly includes a check valve in the neck and said method further includes automatically opening the check valve upon drawing the vacuum in the waste collection unit to allow the medical waste to enter the waste collection unit and closing the check valve when the vacuum ceases to be drawn in the waste collection unit to prevent the medical waste from entering the waste collection unit.

4. A method of collecting medical waste in a waste collection unit having a waste inlet for receiving the medical waste, said method comprising the steps of:
   providing a disposable manifold and filter assembly including:
      a manifold housing having a manifold bottom wall and a manifold peripheral wall, the manifold housing defining a chamber and at least one inlet;
      a neck disposed on the manifold bottom wall and extending downwardly therefrom to define at least one outlet; and
      a filter basket mounted in the chamber between the at least one inlet and the at least one outlet, the filter basket having: a basket bottom wall with a first plurality of openings; a basket peripheral wall with a second plurality of openings; and an imperforate wall section between the first and second plurality of openings to define a space for waste storage between the first and second plurality of openings; and
      a plurality of spacers disposed between the manifold housing and the filter basket such that the basket bottom wall is spaced from the manifold bottom wall and the basket peripheral wall is spaced from the manifold peripheral wall to define a fluid bypass between the manifold housing and the filter basket;
   inserting the neck of the disposable manifold and filter assembly into the waste inlet of the waste collection unit to direct the medical waste passing through the disposable manifold and filter assembly into the waste collection unit;
   connecting at least one tube to the at least one inlet of the manifold housing to provide a path for the medical waste to travel from a target site to the disposable manifold and filter assembly; and
   drawing a vacuum in the waste collection unit to pull the medical waste through the at least one tube and into the disposable manifold and filter assembly where the medical waste is processed in a plurality of stages including a first stage in which the medical waste is filtered through the first plurality of openings in the basket bottom wall until the basket bottom wall becomes plugged with filtered-out material and the medical waste rises to fill the space for waste storage defined by the imperforate wall section, a second stage, following the first stage, in which the medical waste is filtered through the second plurality of openings in the basket peripheral wall until the basket peripheral wall becomes plugged with filtered-out material and the medical waste rises to the fluid bypass, and a third stage, following the second stage, in which the medical waste enters the fluid bypass to bypass the filter basket.

\* \* \* \* \*